May 2, 1967 E. S. BOERNER Plant Pat. 2,735
CHRYSANTHEMUM PLANT
Filed April 22, 1966
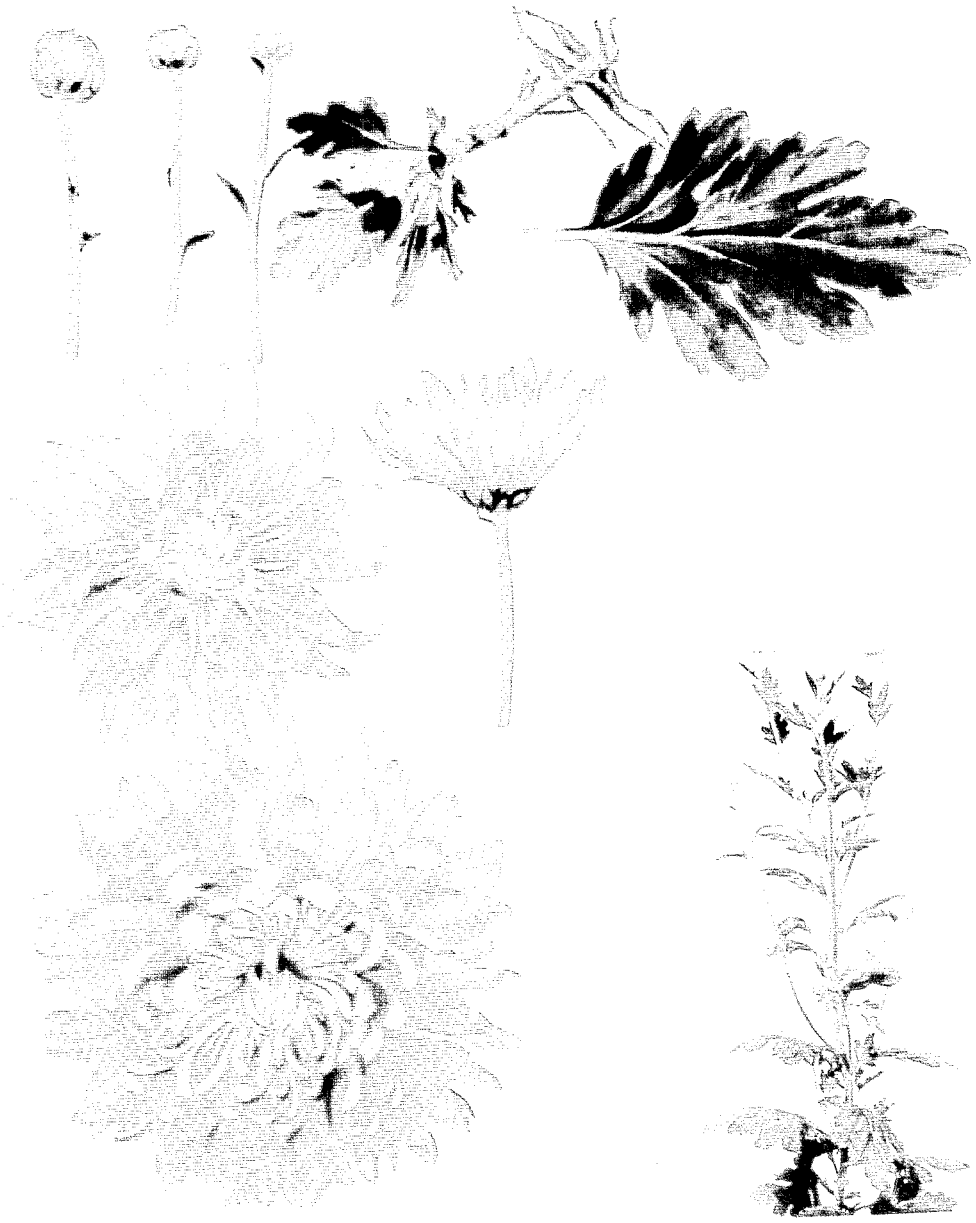
Inventor.
E. S. Boerner
By: Robb & Robb
attorneys.

United States Patent Office

Plant Pat. 2,735
Patented May 2, 1967

2,735
CHRYSANTHEMUM PLANT

Eugene S. Boerner, Newark, N.Y., assignor to Jackson & Perkins Company, Newark, N.Y., a corporation of New York Filed Apr. 22, 1966, Ser. No. 544,634
1 Claim. (Cl. Plt.—82)

The present invention relates to a new and distinct variety of chrysanthemum plant of the reflexed class with incurved center, which was originated by me by crossing an unnamed and unpatented seedling of "Meadowlark" (Plant Patent No. 1,305) × "Thrush" (Plant Patent No. 1,168) with the variety "Cockatoo" (Plant Patent No. 1,171).

The primary objective of this breeding was to produce a new crysanthemum variety which combines the large flower size of the variety "Golden Cockatoo" (Plant Patent No. 1,638) with the strength and vigor of the unnamed seedling parent aforesaid. This objective was fully achieved, along with other desirable improvements, as evidenced by the following unique combination of characteristics which are outsanding in the new variety and distinguish it from its parents, as well as from all other varieties of which I am aware:

(1) A free and vigorous habit of growth;
(2) Large size of the blooms;
(3) A reflexed flower form, with an incurved center; and
(4) A distinctive and attractive general color tonality of the flowers corresponding to Scarlet-Red, very lightly overcast with Nopal Red.

Asexual reproduction of the new variety by both top cuttings and underground runners, as performed at Newark, N.Y., shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature:

Parentage: Seedling.
*Seed parent.*—An unnamed seedling of "Meadowlark" × "Thrush."
*Pollen parent.*—"Cockatoo."
Classification: Reflexed, with incurved center.
Growth: From 18 inches to 24 inches tall.
Locations where observations made: Outdoors at Newark, N.Y., near mid-morning during the early part of the month of October.

Cold resistance: Winter hardy in northern New York State.
Blooming period: In Newark, N.Y. climatic area, bloom begins in late September and continues until severe frosts.

*Flower*

Bud:
*Color.*—When petals first divide—Acajou Red, Plate 13. When petals begin to unfurl—Pomegranate Purple, Plate 12, very lightly overcast with Rose Red, Plate 12. When half blown: inside—Spectrum Red, Plate 1; outside—Mustard Yellow, Plate 16, with upper half of petal lightly overcast with Rose Doree, Plate 1.
*Peduncle.*—Color—Biscay Green, Plate 17. Strength strong.

Bloom:
*Size.*—5½ inches.
*Stem.*—Stiff.
*Form.*—Outer petals reflexed, with center incurved.
*Petalage.*—Double.
*Color.*—Center of flower—Nopal Red, Plate 1, very lightly overcast with Spectrum Red, Plate 1, with reverse of petals Pale Yellow-Orange, Plate 3, very lightly overcast with Rose Doree, Plate 1. Outer petals—Scarlet-Red, Plate 1. Base of petals—Strontian Yellow, Plate 16. Inside of petals—Scarlet-Red, Plate 1, very lightly overcast with Nopal Red, Plate 1. Reverse of petals—Light Orange-Yellow, Plate 3, with upper half of petals faintly overcast with Geranium Pink, Plate 1.
*Petals.*—Texture—velvety. Form—oval.
*Fragrance.*—Characteristic chrysanthemum.

*Plant*

Form: Upright.
Growth: Free; vigorous.
Foliage:
*Size.*—Medium.
*Quantity.*—Normal.
*Color.*—Upper side—Leaf Green, Plate 41. Reverse side—Light Elm Green, Plate 17.
*Texture.*—Leathery.

I claim:

A new and distinct variety of chrysanthemum plant of the reflexed class with incurved center, substantially as herein shown and described, characterized particularly as to novelty by the unique combination of a free and vigorous habit of growth, large bloom size, a reflexed flower form with incurved center, and a distinctive and attractive general color tonality of the flowers corresponding to Scarlet-Red, very lightly overcast with Nopal Red.

No references cited.

ANTONIO F. GUIDA, *Acting Primary Examiner.*
ROBERT E. BAGWILL, ABRAHAM G. STONE, *Examiners.*